United States Patent [19]

Theodorou

[11] Patent Number: 4,967,742

[45] Date of Patent: Nov. 6, 1990

[54] PORTABLE BREATHING DEVICE

[76] Inventor: Ignatius E. Theodorou, 4 Kippy Dr., Newton, Mass. 02168

[21] Appl. No.: 24,016

[22] Filed: Mar. 10, 1987

[51] Int. Cl.[5] .................... A61M 15/00

[52] U.S. Cl. .................... 128/202.13; 128/202.27

[58] Field of Search .................... 128/205.13, 205.17, 128/205.19, 203.19, 202.13, 201.19, 201.11, 205.24, 205.21, 200.27, 200.28, 201.22-201.26, 201.28, 201.29, 202.19, 202.14, 203.28, 204.26, 204.28, 205.12, 265.16, 265.25, 206.15, 202.26, 206.17, 206.21, 206.28, 206.29, 207.12

[56] References Cited

U.S. PATENT DOCUMENTS

| | | | |
|---|---|---|---|
| 26,477 | 2/1865 | Lane | 128/202.19 |
| 125,515 | 4/1872 | Ball | 128/201.23 |
| 396,809 | 1/1889 | Cochran | 128/201.23 |
| 693,795 | 2/1902 | Giersberg | 128/205.17 |
| 996,739 | 7/1911 | Vinton | 128/201.43 |
| 1,009,083 | 11/1911 | McNamee | 128/205.13 |
| 2,535,938 | 12/1950 | Lombard | 128/205.17 |
| 2,737,177 | 3/1956 | Anklin | 128/205.13 |
| 3,045,671 | 7/1962 | Updegraff | 128/205.21 |
| 3,070,089 | 12/1962 | Dick | 128/205.13 |
| 3,105,488 | 10/1963 | Richards | 128/205.13 |
| 3,548,822 | 12/1970 | Seeler | 128/203.11 |
| 4,226,233 | 10/1980 | Kritzer | 128/205.13 |
| 4,239,038 | 12/1980 | Holmes | 128/205.13 |
| 4,498,472 | 2/1985 | Tanaka | 128/203.28 |
| 4,754,751 | 7/1988 | Mauszelle et al. | 128/201.25 |
| 4,757,813 | 7/1988 | Haydu | 128/201.23 |

*Primary Examiner*—Randall L. Green
*Assistant Examiner*—K. M. Reichle
*Attorney, Agent, or Firm*—Edward A. Gordon

[57] ABSTRACT

A portable breathing device is disclosed comprising an upper conduit section having an opening in one end to communicate with at least the user's oral passages and a breathing aperture in the other end and a lower flexible and inflatable respiratory gas container section for receiving and containing ambient respiratory gases. The respiratory gas container section has an upper opening communicating with the breathing aperture of the upper section and a lower opening relatively larger than the upper opening for communicating with ambient respiratory gases to thereby permit the user to entrap a volume of ambient respiratory gases within the respiratory gas container section. A seal device is provided for releasably sealing the lower opening of the respiratory gas container section to ensure containment of the entrapped volume of ambient respiratory gases. In the preferred embodiment the upper conduit section is provided with a facial mask adapted to enclose the oral and nasal passages of the user.

8 Claims, 4 Drawing Sheets

PORTABLE BREATHING DEVICE

FIELD OF THE INVENTION

The present invention relates to portable breathing or respiratory devices and more particularly to a portable autonomous breathing device which enables the user to entrap a volume of ambient respirator gas and to breath the entrapped air while in an atmosphere of irrespirable or poisonous gases.

BACKGROUND OF THE INVENTION

Devices for the administration of oxygen and other gases to an individual under various circumstances are manifold. Exemplary of such prior art devices are disclosed in the following U.S. Patent Nos.:

| | | |
|---|---|---|
| 968,306 | Wunderlich | August 23, 1910 |
| 1,203,391 | O'Donnell | October 31, 1916 |
| 2,260,701 | Boothby et al | October 28, 1941 |
| 2,329,289 | Morehouse | September 14, 1943 |
| 2,336,979 | Boothby et al | December 14, 1943 |
| 2,488,261 | Bedini | November 15, 1949 |
| 2,944,546 | Ziherl et al | July 12, 1960 |
| 3,045,672 | Croasdaile | July 24, 1962 |

In still other prior art patents there are disclosed various portable respirators and inhalers. For example, in U.S. Pat. No. 642,057 to Uysdal et al of Jan. 23, 1900 there is disclosed a fireman's portable respirator which is particularly directed to an agent disposed within the breathing bag for absorbing carbonic acid exhaled by the user.

In U.S. Pat. No. 1,449,047 to Johnson of Mar. 26, 1923 there is disclosed a pocket inhalation apparatus which comprises a casing which contains a removable miniature high pressure cylinder bottle for containing a gas and communicating with a series of expansion chambers and an outlet for the gas. In U.S. Pat. No. 3,045,671 to Updegraft of July 24, 1962 there is disclosed a portable inhaler which includes a metal cartridge adapted to retain a supply of gas under high compression.

While such prior art devices provide improvement in the areas intended, there still exists a great need for a portable breathing device which provides a temporary source of respiratory gas to the user while in an atmosphere of irrespirable or poisonous gases.

Accordingly, a principle desirable object of the present invention is to provide a novel portable autonomous breathing device which provides a temporary source of respiratory gas.

Another desirable object of the present invention is to provide a portable breathing device which enables the user to employ ambient on site breathable air or respiratory gases for use in an environment of non-breathable or poisonous gases adjacent the site.

A still further desirable object of the present invention is to provide a temporary inhalation device of compact form when not in use and which is inexpensive to manufacture.

A still further desirable object of the present invention is to provide a portable breathing device which provides in combination a structure having an upper breathing section and an associated lower respiratory gas container section which provides means for containing a volume of ambient respirator gases to provide a temporary supply of respiratory gases to the user when in an atmosphere of irrespirable or poisonous gases.

Another desirable object of the present invention is to provide a temporary breathing device of compact form which can be easily stored at the site of need and which provides for a container of respiratory gas at substantially ambient pressure.

Other desirable objects and advantages of the present invention will in part appear hereinafter and will in part become apparent after consideration of the specification with reference to the drawings.

SUMMARY OF THE INVENTION

In accordance with the present invention there is disclosed a portable autonomous breathing device which comprises an upper section having an opening or aperture in one end to communicate with the user's nasal and oral passages and a breathing opening or aperture in the other end associated with a lower flexible and inflatable respiratory gas container section for receiving and containing ambient respiratory gases. In a preferred embodiment, the respiratory gas container section has an upper opening or aperture communicating with the breathing opening of the upper section and a lower opening or aperture relatively larger than the upper opening for communicating with ambient respiratory gases to thereby permit the user to manually entrap a volume of ambient respiratory gases within the respiratory gas container section. The lower opening of the respiratory gas container section is provided with sealing means to ensure containment of the entrapped volume of ambient respiratory gases. A conduit or tubular means is disposed between the upper section and the respiratory gas container section to permit passage of gases therebetween. In one embodiment of the invention a one-way check valve means is disposed in the conduit to permit respiratory gases to flow from the lower gas container section to the upper mask section during inhalation of the user. In another embodiment an additional one-way check valve means is provided in the conduit to permit exhalation gases to pass from the user to the respiratory gas container.

BRIEF DESCRIPTION OF THE DRAWINGS

For a fuller understanding of the nature and desired objects of the invention, reference should be had to the following detailed description taken in connection with the accompanying drawings wherein like reference characters denote corresponding parts throughout the several views and wherein.

DETAILED DESCRIPTION OF PREFERRED EMBODIMENTS

Figure 1:
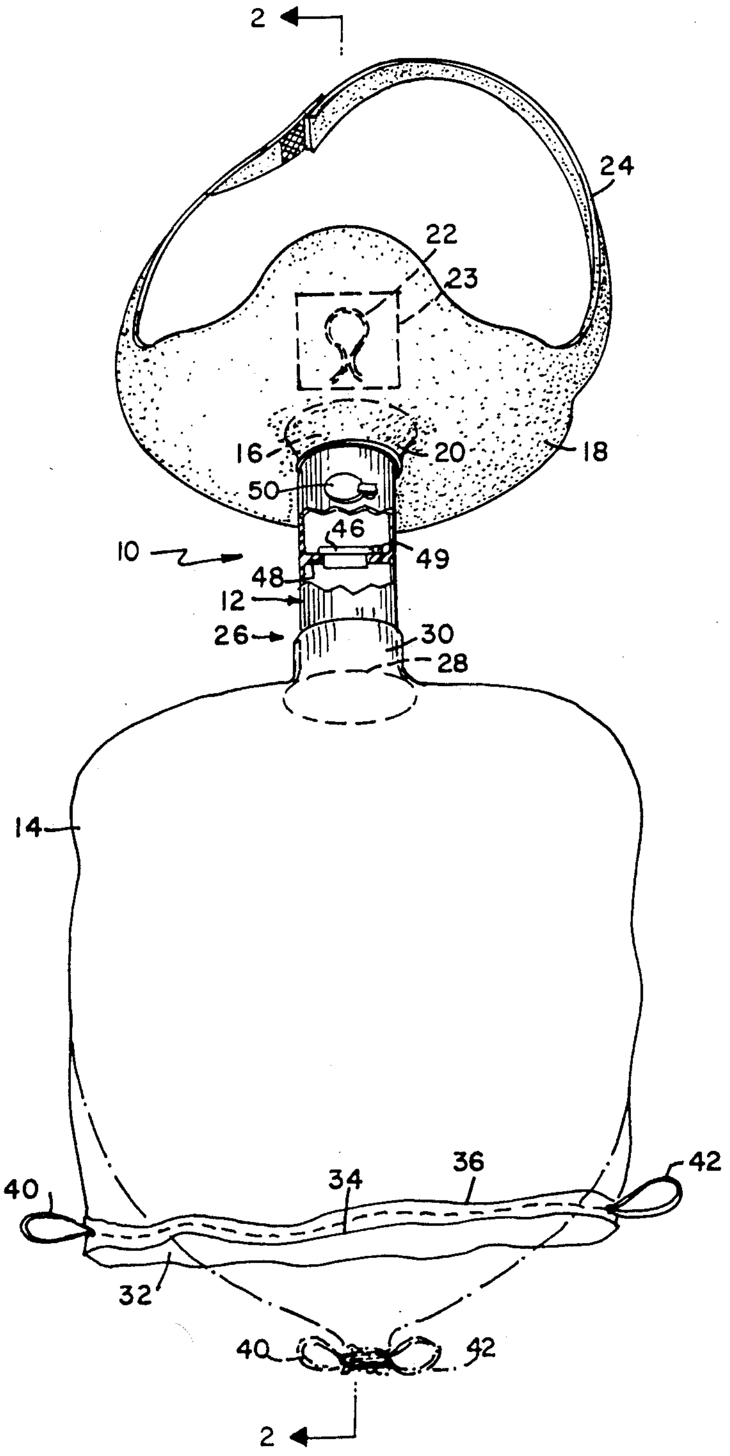
FIG. 1 is a front elevation view of a portable breathing device in accordance with the present invention.
Figure 2:
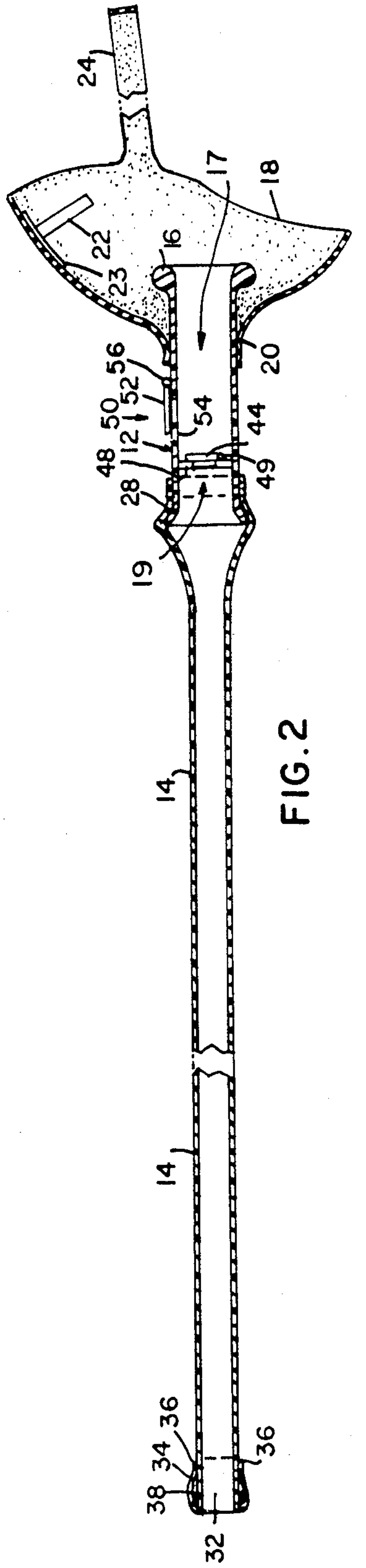
FIG. 2 is a sectional view along the line 2—2 of FIG. 1.
Figure 3:
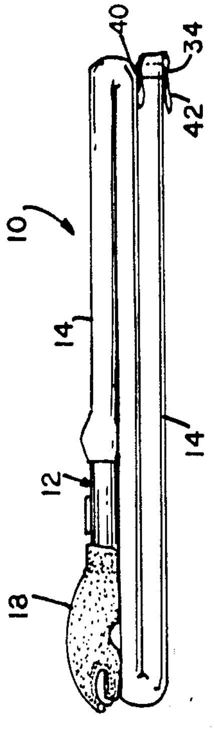
FIG. 3 is a side elevation view of the portable breathing device of FIG. 1 in the packed or stowable configuration.

Referring now to the drawings and more particularly to FIGS. 1-3 there is illustrated generally at 10 a portable breathing device in accordance with the present invention. The breathing apparatus 10 comprises two main sections, namely an upper breathing conduit section 12 and a lower respiratory gas container section 14 associated with section 12. Section 12 is preferably tubular in configuration and is open at its upper end to communicate with the oral breathing passages of the user. The upper end of conduit section 12 is preferably provided with a flange 16 defining a first or upper aperture or opening 17 as best seen in FIG. 2 to form a mouth piece member to enable the user to hold the breathing section securely in position in the user's mouth. The upper breathing section 12 is preferably formed of a plastic material such as polyvinyl chloride extruded in tubular form and of sufficient thickness to ensure that the tube remains open and is not easily collapsed. In the embodiment illustrated, the upper section 12 is provided with a face mask member 18 which can also be formed of a thin sheet of transparent plastic material such as polyvinyl chloride which can be heat sealed to the breathing section 12 at area 20. The mask member is provided with nose clamp means 22 secured to the inner side of the mask 18 by a suitable attaching means 23 such as adhesives, mating members such as "VELCRO" strips, double backed adhesive tapes and the like well known to those skilled in the art. The mask member 18 is applied to the face so that the mouth piece flange 16 is inserted into the mouth and the nose clamp applied to the user's nose. The mask is held in position (similar to that shown in FIG. 5) by a suitable head strap 24 which may be elastic or plastic straps secured together by means such as mating VELCRO strips described above.

The lower respiratory gas container section 14 is preferably formed of lightweight relatively thin, flexible unitary sheet of gas and fluid impervious plastic material such as polyethylene or polyvinyl chloride described above. The respiratory gas container 14 is preferably shaped at its upper end 26 to conform to the flanged end 28 defining a second or lower aperture or opening 19 as best seen in FIG. 2 of section 12 and is attached thereto at area 30 of section 12 by suitable means such as heat sealing or adhesives to form an air tight seal. The other end of the respiratory container 14 is provided with an opening 32 which is substantially larger than the upper opening 28 and is defined by the edge 34. The plastic material of edge 34 is preferably turned outwardly and sealed such as by heat-sealing along the edge shown by the line 36 to form an internal channel 38 to receive draw string members 40 and 42 which secure, close and seal the openings 32 (as shown by the dotted lines of FIG. 1) to ensure containment of an entrapped volume of ambient respiratory gases as described hereinafter with respect to operation of the portable respirator device of the present invention.

Mounted in the breathing section member 12 is a suitable valve means 44 such as a one-way check valve having a disk 46 which normally seats upon a valve seat 48 and opens into the mouth piece area 20 and the mask 18 when the user inhales thereby causing the disk 46 to swing open on its hinge 49. A similar one-way check valve 50 is mounted in the wall of section 12 between the mouth piece flange 16 and valve 44 and comprises a disk 52, seat 54 and hinge 56. The disk 52 normally opens to the ambient atmosphere when pressure caused by the user's exhalation contacts the disk. Similarly the user's exhalation pressure causes disk 46 of valve 44 to close thereby preventing exhaled gases from entering the lower respiratory gas container section 14.

Figure 4:
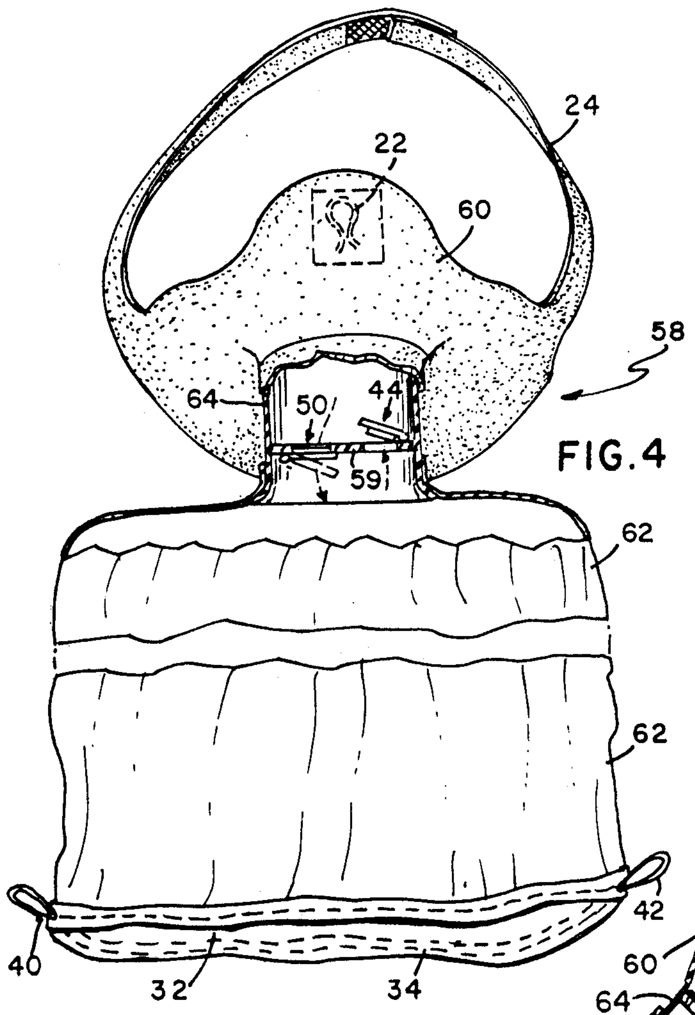
FIG. 4 is a front elevation view partly in section of a modified embodiment of the portable breathing device of the present invention.
Figure 5:
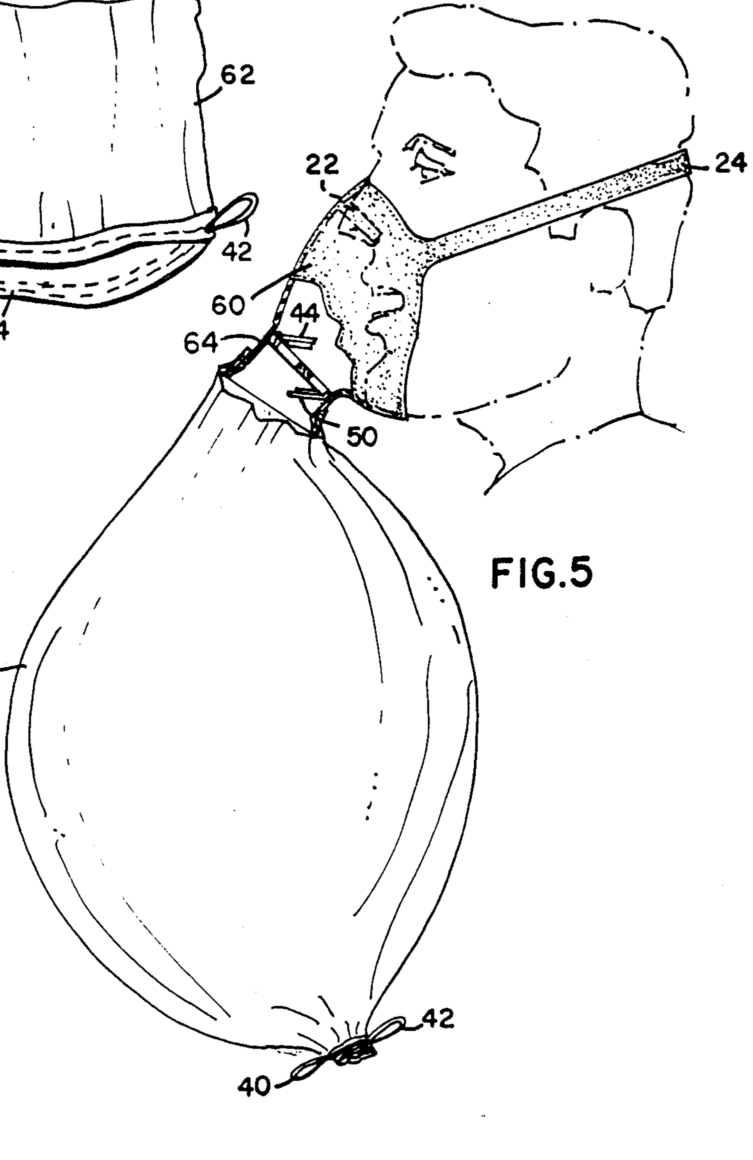
FIG. 5 is a side elevation view of the portable breathing device of FIG. 4 and also showing the device in use.

Referring now to FIGS. 4 and 5, there is illustrated a modified embodiment of the portable respiratory device of the present invention shown generally at 58. In this embodiment the face mask 60 is constructed to cover the oral and nasal (oronasal) passages of the user's face as best seen in FIG. 5. Additionally in this embodiment the respiratory device 58 is a unitary structure of the face mask section 60 attached to the upper portion of intermediate conduit member 64 which contains check valves 44 and 50 and the respiratory gas container 62 which is attached to the lower portion of the conduit member 64 and is formed of a plastic material such as polyvinyl chloride as described above with respect to FIGS. 1 and 2 except that the exhaled gases of the user are directed through one-way check valve 50 into the respirator gas container 62 to mix with and dilute the entrapped respiratory gases contained therein. As mentioned, in this embodiment of the invention, the exhalation gases which are conducted into the respiratory gas container through check valve 50 serve to dilute the entrapped respiratory gases and thereby extends the useful time of the breathing device for a given volume of entrapped respiratory gases which are inhaled by the user through one-way check valve 44. As illustrated in FIGS. 4 and 5 and the valves 44 and 50 are mounted adjacent to each other in the same plane within the conduit section 64.

Referring now to FIGS. and 7, there is illustrated a modified embodiment of the invention. As shown, the portable breathing device comprises a respiratory gas container section 66 having an opening 68 at one end and which serves as an inflatable gas reservoir. The respiratory gas container is preferably formed of fluid impervious plastic material as described hereinbefore. The edge 70 of the opening 68 is formed into a channel 72 to receive securing means such as draw string members 74 and 76 which releasably close, secure, and seal the opening 68 about the breathing conduit member 78 after the respiratory container section 66 has been filled with respiratory gases. The breathing conduit member 78 is attached to a portion of the inner surface 80 of gas container 66 by suitable attaching means 82 and 84 which may, for example, be mating "VELCRO" strips or suitable adhesive tapes and the like as is well known. The breathing conduit 78 is preferably formed of a tubular plastic material such as described with respect to breathing section 12 of FIG. 1 and is provided with a one-wa normally closed check valve 86 which is identical in construction to valve 44 of FIGS. 1 and 2. The upper end of the breathing conduit 78 is provided with a face mask 88 having a head strap 90. The valve 86 remains open so long as the wearer of the mask is inhaling and taking in the gaseous supply from respiratory container section 66. However, when the wearer exhales, valve 86 is closed by the exhalation pressure, and the exhaled gases exit through one-way check valve 92 which is normally closed but is opened by the exhalation pressure. The valve 92 is identical in construction to valve 50 of FIG. 1. FIG. 7 shows the portable respiratory device of FIG. 6 in the inflated ready to use mode.

Figure 8:
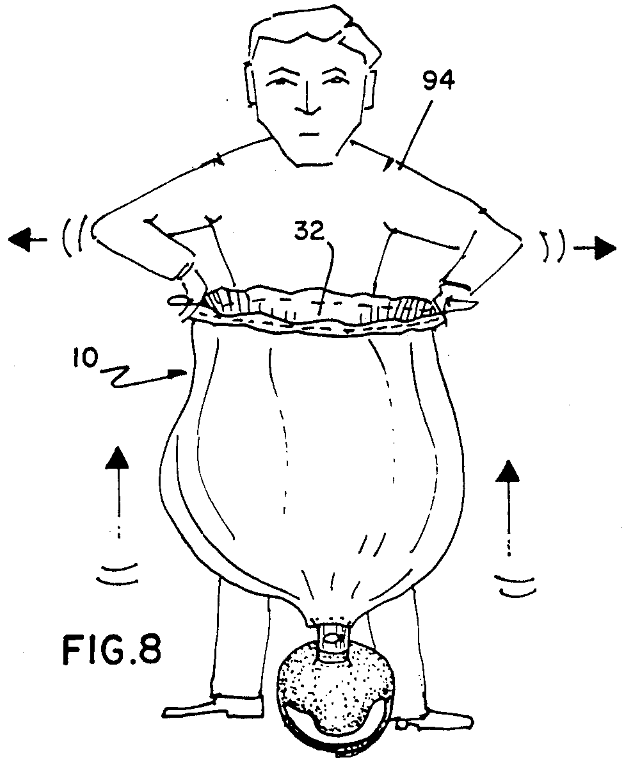
FIG. 8 is a perspective view illustrating the user entrapping respiratory gases within the respiratory gas container of the present invention as illustrated in FIG. 1.

When not in use the breathing device of the present invention can, for example, when in the folded form illustrated in FIG. 3, be stored in each office of an office building in sufficient quantities to serve the occupants of each office. To use the portable breathing device, in the event of an emergency such as fire and where it is necessary to cross an area of irrespirable or poisonous gases in order to escape to a safe area, the user unfolds the portable breathing device and with the end 32 of the respirator gas container 10 (FIG. 1) open fills the container with ambient breathable respiratory gases by suitable arm movement of the user 94 to inflate the respiratory container as shown in FIG. 8. The opening 32 is then sealed by means of sealing members 40 and 42 to thereby ensure containment of the entrapped gases. The face mask 18 and mouth piece 16 are then positioned for use whereby the user has a supply of breathable respiratory gases while passing safely through the area of harmful ambient gases and smoke.

Figure 6:
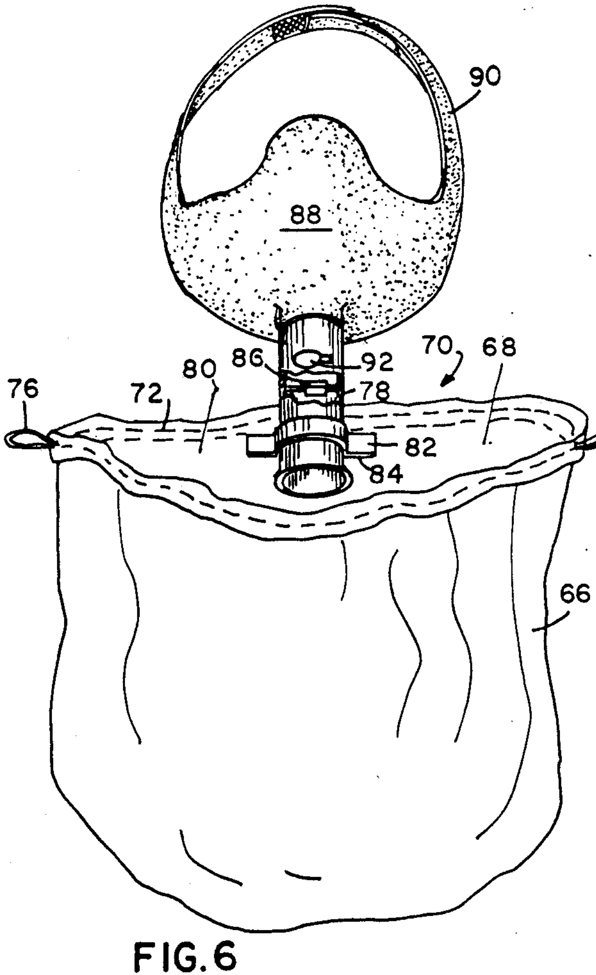
FIG. 6 is an elevation view of a modified embodiment of the invention.
Figure 7:
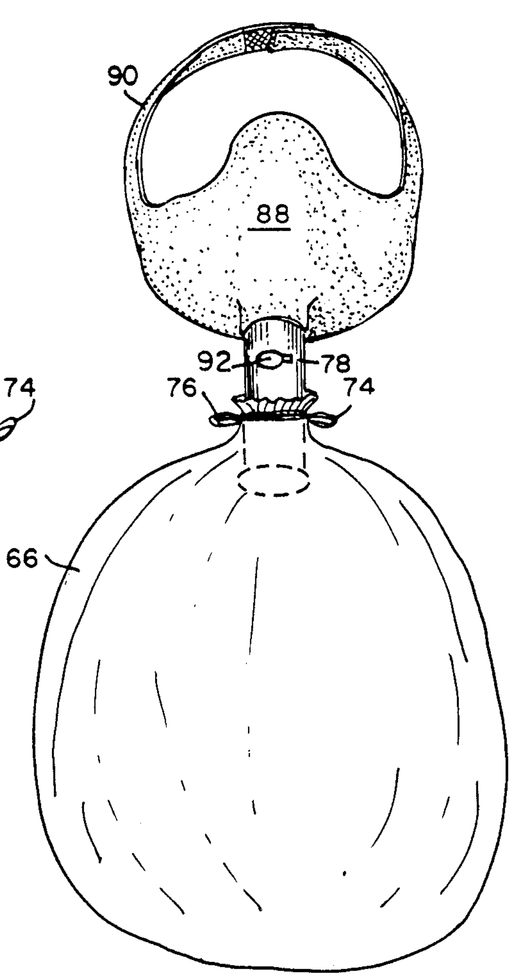
FIG. 7 is a perspective view of the portable breathing device of FIG. 6 in the inflated mode.

The portable respiratory device illustrated in FIGS. 6 and 7 is employed in the same manner as described above with respect to the embodiment set forth in FIGS. 1-3.

One feature of the present invention is that the complete portable respiratory device of the present invention may be folded and stored in a small area or packaged in a small sized container such as a handbag or desk drawer.

An important feature of the portable breathing apparatus of the present invention is that the gas pressure within the filled respiratory gas container is generally at a gas pressure which is equal to or slightly greater than the ambient atmospheric pressure and therefore is self-regulating i.e. the respiratory gases are withdrawn by inhalation i.e. "on demand" by the user rather than the continuous flow involved with high pressure containers and associated valves to control the flow as employed by the prior art devices. Additionally, since the respiratory gas container while in use is always at ambient atmospheric pressure, the possibility of exchange between ambient gases and respiratory gases contained within the gas container is substantially completely eliminated. The portable breathing apparatus of the present invention may be quickly and easily refilled from an ambient source of respiratory gases to provide an extended supply of respiratory gases.

It is to be understood that modifications of the illustrated embodiments of the present invention can be made within the scope of the invention. For example, the embodiments of FIGS. 1 and 7 can be employed without the facial masks 18 and 86. In such a modification the conduit sections 12 and 78 are provided with only the valve means 44 and 86 respectively to thereby permit the user to orally inhale respiratory gases from the respiratory gas container and exhale to the ambient area through the user's nasal passages. Additionally, in a modified embodiment (not shown), the face mask can be adapted to cover the users eyes as well as the oral and nasal passages.

It has been determined that a portable breathing device in accordance with the present invention having a 30 gallon respiratory container will provide a source of respiratory gases for between about 3 to 5 minutes.

It is believed apparent that the portable breathing device of the present invention provides a temporary, reusable atonomous breathing device which is particularly suitable for emergency situations and which can be easily stored in various locations ready for instant use with a minimum of preparation, and which is highly economical to produce.

While the invention has been described with respect to preferred embodiments, it will be apparent to those skilled in the art that changes and modifications may be made without departing from the scope of the invention herein involved in its broader aspects. Accordingly, it is intended that all matter contained in the above description, or shown in the accompanying drawing shall be interpreted as illustrative and not in a limiting sense.

What is claimed is:

1. A portable autonomous breathing device comprising:

an upper respiratory gas conduit section having a first aperture at one end adapted to communicate with at least the oral passages of a user and a second aperture at the other end adapted to receive respiratory gases;

a facial mask member attached about the first aperture of said conduit section;

a lower inflatable respiratory gas container section for receiving and containing ambient respiratory gases at ambient atmospheric pressure;

said respiratory gas container section having an upper opening fluidically communicating with the second aperture of said upper conduit section and a continuous flexible edge portion defining a lower opening relatively larger than said upper opening for communicating with ambient respiratory gases thereby permitting the user to manually entrap a volume of ambient respiratory gases within said respiratory gas container section at ambient atmospheric pressure;

means for releasably sealing at ambient atmospheric pressure said lower opening of said respiratory gas container section to contain the manually entrapped volume of ambient respiratory gases at ambient atmospheric pressure;

a first valve means mounted within the conduit section between the first and second apertures permitting inhalation of respiratory gases therethrough; and a second valve means mounted in the wall of the conduit section between the first valve means and the first aperture of the conduit section permitting exhalation gases to pass therethrough to the ambient atmosphere and resistant to inhalation of ambient atmosphere therethrough.

2. The portable autonomous breathing device of claim 1 wherein said mask member and lower respiratory gas container section are formed of a flexible material whereby said breathing device is foldable for storage at the site of use.

3. A portable autonomous breathing device adapted for entrapping ambient respiratory gases for a user comprising:

a gas impervious inflatable respiratory gas container member having a continuous flexible edge portion defining an upper opening providing access to the inner surface of said container member thereby permitting the user to manually entrap a volume of ambient respiratory gases within said gas container member at ambient atmospheric pressure;

a conduit member having a first aperture at the upper end and a second aperture at the lower end;

a facial mask member attached about the first aperture of the upper end of the conduit member and adapted to enclose the oral and nasal passages of the user;

means for releasably sealing the continuous flexible edge portion of said upper gas container member opening about the second aperture of the lower end of said conduit member to contain the manually entrapped volume of ambient respiratory gases within the respiratory gas container at ambient atmospheric pressure;

a first valve means mounted within the conduit member between the first and second apertures permitting inhalation of respiratory gases therethrough and resistant to passage of exhalation gases therethrough; and a second valve means mounted in the wall of the conduit member between the first valve means and the first aperture of the conduit member permitting exhalation gases to pass therethrough to the ambient atmosphere and resistant to inhalation of ambient atmosphere therethrough.

4. The portable breathing device of claim 3 wherein said facial mask member and respiratory gas container member are formed of a flexible material whereby said breathing device is foldable for storage at the site of use.

5. A portable breathing device adapted for entrapping ambient respiratory gases at ambient atmospheric pressure for a user comprising:

a gas impervious inflatable respiratory gas container having a continuous flexible edge portion defining an upper opening providing access to the inner surface of said container thereby permitting the user to manually entrap a volume of ambient respiratory gases within said gas container at ambient atmospheric pressure;

a conduit member attached to the inner surface of said respiratory gas container adjacent said upper opening thereof;

said conduit member having a first aperture external to said respiratory gas container and a second aperture disposed within said gas container;

means for releasably sealing the continuous flexible edge portion of the respiratory gas container opening about said conduit member to contain the manually entrapped volume of ambient respiratory gases at ambient atmospheric pressure; and valve means mounted in said conduit member to permit inhalation of entrapped respiratory gases from said respiratory gas container.

6. A portable autonomous breathing device comprising:

an upper respiratory gas conduit section having a first aperture at one end adapted to communicate with at least the oral passages of a user and a second aperture at the other end adapted to receive respiratory gases;

a lower flexible and inflatable respiratory gas container section for receiving and containing ambient respiratory gases at ambient atmospheric pressure;

said respiratory gas container section having an upper opening fluidically communicating with the second aperture of said upper conduit section and a flexible edge defining a lower opening relatively larger than said upper opening for communicating with ambient respiratory gases whereby the respiratory container section may be extended under ambient atmospheric pressure to permit the user to manually entrap a volume of ambient respiratory gases within said respiratory gas container section under ambient atmospheric pressure; and means for releasably sealing at ambient atmospheric pressure the lower opening of the respiratory gas container section to prevent the manually entrapped volume of ambient gases at ambient atmospheric pressure from passing outwardly through said lower opening, and prevent ambient gases from passing inwardly through said lower opening.

7. The portable autonomous breathing device of claim 6 further comprising valve means disposed in said conduit section to control passage of gases therethrough.

8. A portable autonomous breathing device comprising:

an upper respiratory gas conduit section having a first aperture at one end adapted to communicate with at least the oral passages of a user and a second aperture at the other end adapted to receive respiratory gases;

a facial mask member attached about the first aperture of said conduit section;

a lower inflatable respiratory gas container section for receiving and containing ambient respiratory gases at ambient atmospheric pressure;

said respiratory gas container section having an upper opening fluidically communicating with the second aperture of said upper conduit section and a continuous flexible edge portion defining a lower opening relatively larger than said upper opening for communicating with ambient respiratory gases thereby permitting the user to manually entrap a volume of ambient respiratory gases within said respiratory gas container section at ambient atmospheric pressure;

means for releasably sealing at ambient atmospheric pressure said lower opening of said respiratory gas container section to contain the manually entrapped volume of ambient respiratory gases at ambient atmospheric pressure; and first and second valve means mounted adjacent to each other in the same plane within said upper respiratory gas conduit section;

said first valve means permitting inhalation of respiratory gases therethrough from said respiratory gas container and inhibiting passage of exhalation gases therethrough;

said second valve means permitting exhalation gases to pass therethrough to said respiratory gas container to thereby dilute the contained respiratory gases and thereby extend the useful breathing time of said device for a given volume of entrapped respiratory gases.

* * * * *